United States Patent [19]

Cullinan et al.

[11] Patent Number: 4,479,957

[45] Date of Patent: Oct. 30, 1984

[54] USE OF VINDESINE IN TREATING ACUTE LYMPHATIC LEUKEMIA AND OTHER SUSCEPTIBLE NEOPLASMS

[75] Inventors: George J. Cullinan, Trafalger; Koert Gerzon, Indianapolis, both of Ind.

[73] Assignee: Eli Lilly and Company, Indianapolis, Ind.

[21] Appl. No.: 250,459

[22] Filed: Apr. 2, 1981

Related U.S. Application Data

[60] Continuation of Ser. No. 101,335, Dec. 6, 1979, abandoned, which is a continuation-in-part of Ser. No. 935,828, Aug. 22, 1978, abandoned, which is a division of Ser. No. 828,693, Aug. 29, 1977, abandoned, which is a continuation-in-part of Ser. No. 721,650, Sep. 8, 1976, abandoned, which is a continuation-in-part of Ser. No. 539,681, Jan. 9, 1975, abandoned, which is a continuation-in-part of Ser. No. 446,869, Feb. 28, 1974, abandoned, which is a continuation-in-part of Ser. No. 347,275, Apr. 2, 1973, abandoned.

[51] Int. Cl.$^3$ .......................................... A61K 31/475
[52] U.S. Cl. .................................................... 424/262
[58] Field of Search ......................................... 424/262

[56] References Cited

PUBLICATIONS

Cancer, Sierocki, et al., Carcinoma Metastatic to the Anterior Ocular Segment: Response to Chemotherapy, vol. 45, No. 10, 1980, pp. 2521-2523.
Anticancer Research, Weber et al., The Evaluation of Neurotoxicity in Cancer Patients Treated with Vinca Alkaloids with Special Reference to Vindesine, 1:31-34(1981) pp. 31-34.
Anticancer research, Mathe, et al., Phase II Clinical Trials with Vindesine in Patients with Hematologic Malignancies, 1:1-9, (1981), pp. 1-9.
Cancer, Vats, et al., Vindesine and Prednisone for Remission Induction in Children with Acute Lymphocytic Leukemia, vol. 47, No. 12, Jun. 15, 1981, pp. 2789-2792.
Europ. J. Cancer, Houwen, et al., Vindesine Therapy in Melphalan-Resistant Multiple Myeloma, vol. 17, 1981, pp. 227-232.
Proceedings of the International Vinca Alkaloid Symposium-Vindesine (Symposium), Frankfurt, Germany, Nov. 1980, Table of Contents, pp. 159-170; 214-220; 289-312; 422-429.
Cancer Chemotherapy and Pharmacology—Vindesine International Workshop—vol. 2, pp. 29-274 (1979).
Current Chemotherapy pp. 1328-1331; 1331-1334; 1334-1336 (1978).
Cancer Treatment Reports, 61, pp. 1727-1729 (1977); 62, pp. 805-809, 1427-1433(1978); 63, pp. 1343-1346; 2019-2021; 2063-2065; 2097-2098(1979).
Vindesine Bibliography
Barnett et al., J. Med. Chem., 21, 88 (1978).

*Primary Examiner*—Jerome D. Goldberg
*Attorney, Agent, or Firm*—James L. Rowe; Arthur R. Whale

[57] ABSTRACT

This invention relates to a method of treating neoplasms which comprises administering to a mammal suffering from a vindesinesusceptible neoplasm selected from the group consisting of acute lymphatic leukemia, acute granulocytic leukemia, chronic myeloid leukemia, non-small cell lung cancer, Hodgkin's disease, non-Hodgkin's lymphoma, malignant melanoma carcinoma of the breast, esophageal carcinoma and testicular carcinoma an anti-neoplastically-effective amount of vindesine or a pharmaceutically-acceptable acid addition salt thereof.

5 Claims, No Drawings

USE OF VINDESINE IN TREATING ACUTE LYMPHATIC LEUKEMIA AND OTHER SUSCEPTIBLE NEOPLASMS

CROSS-REFERENCE

This application is a continuation of our copending application Ser. No. 101,335 filed Dec. 6, 1979, now abandoned which was a continuation-in-part of our copending application Ser. No. 935,828 filed Aug. 22, 1978 now abandoned which was a division of our then copending Ser. No. 828,693 filed Aug. 29, 1977, now abandoned, which was a continuation-in-part of our then copending application Ser. No. 721,650 filed Sept. 8, 1976 now abandoned, which was a continuation-in-part of our then copending application Ser. No. 539,681, filed Jan. 9, 1975, now abandoned, which was in turn a continuation-in-part of our then copending application Ser. No. 446,869 filed Feb. 28, 1974, now abandoned, which was in turn a continuation-in-part, of our then copending application, Ser. No. 347,275 filed Apr. 2, 1973, now abandoned.

BACKGROUND OF THE INVENTION

Several naturally-occurring alkaloids obtainable from *Vinca rosea* have been found active in the treatment of experimental malignancies in animals. Among these are leurosine (U.S. Pat. No. 3,370,057), vincaleukoblastine (vinblastine) to be referred to hereinafter as VLB (U.S. Pat. No. 3,097,137), leurosidine (vinrosidine) and leurocristine (VCR or vincrisitine) (both in U.S. Pat. No. 3,205,220), deoxy VLB "A" and "B", *Tetrahedron Letters*, 783 (1958) desacetyl leurosine hydrazide is also disclosed therein); 4-desacetoxy vinblastine (U.S. Pat. No. 3,954,773; 4-desacetoxy-3'-hydroxyvinblastine (U.S. Pat. No. 3,944,554); leurocolombine (U.S. Pat. No. 3,890,325) and vincadioline (U.S. Pat. No. 3,887,565). Two of these alkaloids, VLB and leurocristine, are now marketed as drugs for the treatment of neoplasms, VLB for the palliative treatment of lymphomas, generalized Hodgkin's disease, lymphosarcoma, reticulum-cell sarcoma, mycosis fungoides, neuroblastoma, Letterer-Siwe disease, choriocarcinoma, carcinoma of the breast, and embryonal carcinoma of the testis. Vincristine is indicated in the treatment of acute leukemia, and in combination with other oncolytic agents, in Hodgkin's disease, lymphosarcoma, reticulum-cell sarcoma, rhabdomyosarcoma, neuroblastoma and Wilm's Tumor.

Chemical modification of the Vinca alkaloids has been rather limited. In the first place, the molecular structures involved are extremely complex and chemical reactions which affect a specific function of the molecule are difficult to develop. Secondly, alkaloids lacking desirable chemotherapeutic properties have been recovered from *Vinca rosea* fractions, and a determination of their structures has led to the conclusion that these compounds are closely related structurally to the antineoplastically-active alkaloids. Thus, antineoplastic activity seems to be limited to very specific structures, and the chances of obtaining more active drugs by modification of these structures would seem to be correspondingly slight. Among the successful modifications of physiologically-active alkaloids has been the preparation of dihydro VLB (U.S. Pat. No. 3,352,868) and the replacement of the acetyl group at C-4 (carbon no. 4 of the VLB ring system-see the numbered structure below) with higher alkanoyl group or with unrelated acyl groups. (See U.S. Pat. No. 3,392,173.) Several of these derivatives are capable of prolonging the life of mice inoculated with P1534 leukemia. One of the derivatives in which a chloracetyl group replaced the C-4 acetyl group of VLB was also a useful intermediate for the preparation of structurally modified VLB compounds in which an N,N-dialkylglycl group replaced the C-4 acetyl group of VLB (see U.S. Pat. No. 3,387,001). An intermediate compound, namely 4-desacetyl VLB, was produced during the chemical reactions leading to these latter derivatives. This intermediate, in which the C-4 acyl group was lacking, leaving an unesterified hydroxy group, has been reported to be a toxic material having little in vivo chemotherapeutic activity against the P1534 murine leukemia system by Hargrove, *Lloydia*, 27, 340 (1964).

A more recent modification has been the replacement of the ester group at C-3 with a carboxamide group. These novel amides are fully described in the parent of this application and in its predecessors—see also Belgian Pat. No. 347,275 issued 10-2-74 and Barnett et al., *J. Med. Chem.*, 21, 88 (1978). One of these amides, 4-desacetyl VLB C-3 carboxamide, generic name vindesine, proposed trademark ELDISINE ®, is undergoing an extensive clinical trial in humans for treatment of acute lymphatic leukemia, acute granulocytic leukemia, chronic myeloid leukemia, non-small cell lung cancer, Hodgkin's disease, non-Hodgkin's lymphoma, malignant melanoma, carcinoma of the breast, esophageal carcinoma and testicular carcinoma.

SUMMARY OF THE INVENTION

This invention provides a method of treating susceptible neoplasms specifically acute lymphatic leukemia, acute granulocytic leukemia, chronic myeloid leukemia, non-small cell lung cancer, Hodgkin's disease, non-Hodgkin's lymphoma, malignant melanoma, carcinoma of the breast, esophageal carcinoma and testicular carcinoma. in mammals which comprises administering vindesine or a pharmaceutically-acceptable salt thereof to a mammal thereof suffering from a vindesine-susceptible neoplasm, in an anti-neoplastically effect amount.

Vindesine is 4-desacetyl VLB C-3 carboxamide and can be represented by the formula

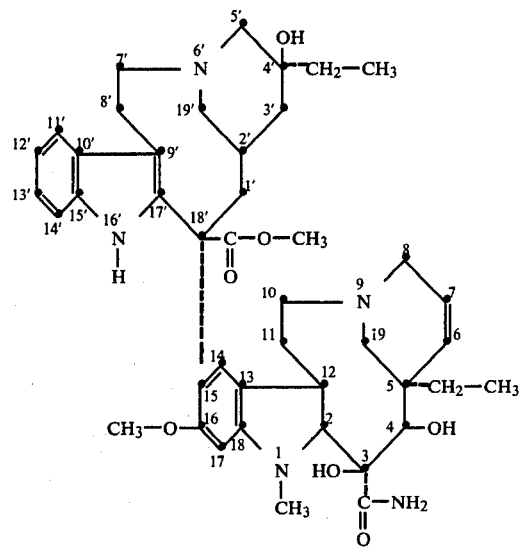

Non-toxic acids useful for forming pharmaceutically-acceptable acid addition salts of vindesine include salts derived from inorganic acids such as: hydrochloric acid, nitric acid, phosphoric acid, sulfuric acid, hydrobromic acid, hydriodic acid, nitrous acid, phosphorus acid and the like, as well as salts of non-toxic organic acids including aliphatic mono and dicarboxylates, phenyl-substituted alkanoates, hydroxy alkanoates and alkandioates, aromatic acis, aliphatic and aromatic sulfonic acids, etc. Such pharmaceutically-acceptable salts thus include the sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptaonate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonates, toluenesulfonate, chlorobenzenesulfonate, xylenesulfonate, phenylacetate, phenylpropionate, phenylbutyrate, citrate, lactate, 2-hydroxybutyrate, glycollate, malate, tartrate, methanesulfonate, propanesulfonate, naphthalene-1-sulfonate, naphthalene-2-sulfonate and the like salts.

Vindesine can be prepared as follows: Treatment of VLB or 4-desacetyl VLB with ammonia yields the corresponding amide. When VLB is the starting material, a mixture of vindesine and VLB C-3 carboxamide is obtained Vindesine thus prepared can be purified by chromatography. Vindesine can also be prepared by this alternate procedure:

4-Desacetyl VLB C-3 carboxhydrazide, prepared by reaction of VLB with anhydrous hydrazine, is transformed into the corresponding azide by treatment with nitrous acid, nitrosyl chloride, nitrogen tetroxide, amyl nitrite or a similar reagent according to conventional procedures. The C-3 azide thus prepared is then reacted with ammonia to yield vindesine.

A second alternative method of preparing vindesine from 4-desacetyl VLB C-3 carboxhydrazide involves the use of a procedure based on that of Ainsworth, U.S. Pat. No. 2,756,235, in which the aforesaid hydrazide is hydrogenolyzed with Raney nickel.

The preparation of vindesine is more fully illustrated in the following specific examples:

EXAMPLE 1

Preparation of Vindesine

About 10 g. of VLB sulfate were converted by standard procedures to VLB free base. The free base, obtained as a residue after evaporation of the dried ethereal solvent, was dissolved in about 200 ml. of anhydrous methanol. Anhydrous liquid ammonia (300 ml.) was added, and the reaction mixture sealed and maintained at about 100° C. for 60 hours. The reaction vessel was opened, and the contents removed and evaporated to dryness in vacuo. The resulting residue, containing vindesine (4-desacetyl VLB C-3 carboxamide), as shown by thin layer chromatography, were combined and the solvent evaporated therefrom in vacuo, yielding as a residue purified vindesine free base. The nmr and ir spectra of the solid free base confirmed the structure indicated. The free base showed a band in the infrared at 1687 cm$^{-1}$, characteristic of the amide function. The molecular weight of the free base determined by mass spectroscopy was 753 which is in agreement with theoretical value calculated for $C_{43}H_{55}N_5O_7$.

600 mg. of the above residue were converted to the sulfate salt by dissolving the free base in aqueous methanol and adjusting the pH of the resulting solution to 2.9 with 1% aqueous sulfuric acid. Evaporation of the reaction mixture to dryness yielded vindesine sulfate which crystallized from an ethanolisopropyl solvent mixture and melted above 250° C. with decomposition. The salt was freely soluble in water.

EXAMPLE 2

4-Desacetyl VLB C-3 carboxhydrazide

4-Desacetyl VLB was heated in anhydrous ethanol with an excess of anhydrous hydrazine in a sealed reaction vessel at about 60° C. for about 18 hours. The reaction vessel was cooled, and opened, the contents removed, and the volatile constituents evaporated therefrom in vacuo. The resulting residue, comprising 4-desacetyl VLB C-3 carboxhydrazide, was taken up in methylenechloride, the methylenechloride solution washed with water, separated and dried, and the methylenechloride removed by evaporation in vacuo. The resulting residue was dissolved in a 1:1 chloroform:benzene solvent mixture and chromatographed over silica gel. The benzene-chloroform-triethylamine eluant of Example 1 was employed to develop the chromatogram. The initial chromatographic fractions contained unreacted 4-desacetyl VLB. Further fractions were found to contain 4-desacetyl 18'-descarbomethoxy VLB C-3 carboxhydrazide previously described by Neuss et al., *Tetrahedron Letters*, 1968, 783. The next fractions, found to contain 4-desacetyl VLB C-3 carboxhydrazide by thin layer chromatography, were combined, and the solvents evaporated therefrom in vacuo. The resulting solid melted at about 219°-220° C. with decomposition. 4-Desacetyl VLB C-3 carboxhydrazide thus prepared had a carbomethoxy absorption band in the IR at 1725-1735 cm$^{-1}$ thereby differentiating it from the 18'-descarbomethoxy compound of Neuss et al. supra, and a 1690 cm$^{-1}$ band in the IR attributable to the hydrazide function. Molecular weight by mass spectrography was 768 in agreement with the theoretical value calculated for $C_{43}H_{56}N_6O_7$. The nmr spectrum contained the prominent resonance at 3.6 ppm representing the methyl group of the C-18 carbomethoxy function.

EXAMPLE 3

Vindesine via 4-Desacetyl VLB C-3 Carboxazide 100 g. of VLB sulfate are dissolved in 1400 ml. of purified water (20°-30° C.) with stirring. 200 ml. of water are used to rinse the sulfate solution into the reaction vessel. 90 ml. of 14 N aqueous ammonium hydroxide are added, thus forming VLB free base. The alkaline aqueous mixture is extracted four times with 500 ml. portions of methylene dichloride. The methylene dichloride extracts are combined and washed with 300 ml. of saturated aqueous sodium chloride. The methylene dichloride solution is dried with anhydrous sodium sulfate, the sodium sulfate is removed by filtration, and the dry methylene dichloride filtrate is evaporated to dryness. VLB free base thus prepared is dissolved in 200 ml. of methanol and the solution plus rinses transferred to a 2-liter 3-neck round bottom flask equipped with stirrer, condenser and thermometer under a nitrogen atmosphere. 225 ml. of hydrazine hydrate are added via a dropping funnel over a 5-minute period. The reaction mixture is left at a temperature in the range 58°–62° C. with stirring for about 16 hours. The reaction mixture is then cooled by addition to an ice-water mixture. The resulting aqueous layer is extracted four times with 900 ml. portions of methylene dichloride. The methylene dichloride extracts are combined and the combined extracts washed with 450 ml. of saturated aqueous sodium chloride and then dried with sodium sulfate. The drying agent is separated by filtration and the filter cake washed with methylene dichloride. The combined filtrate plus washes are then concentrated. The concentrate is placed in a weighed flask using methanol as a rinse and the solvent is removed by evaporation, leaving 4-desacetyl VLB C-3 carboxhydrazide formed in the above reaction as a residue.

About 1500 ml of water are placed in a 4 l. erlenmeyer and the water is chilled to about 10° C. 148 ml. of 12 N aqueous hydrochloric acid are added carefully with stirring. Next, 200 ml. of THF are placed in a one-liter flask to which are added 23 ml. of amyl nitrite. Next, 4-desacetyl VLB C-3 carboxhydrazide prepared as above is dissolved in 1000 ml. of THF and the THF solution placed in a 5 liter round-bottom flask equipped with stirrer, nitrogen inlet (y-tube) and thermometer. The solution is cooled to below about 0° C. About 700 ml. of the previously prepared dilute HCl solution are added. Cooling is continued and when the flask temperature is in the range −3° to −6° C., the previously prepared amyl nitrite solution is added over a 5-minute period. Six to nine minutes later, 625 ml. of 14 N aqueous ammonium hydroxide are added with stirring, thus forming vindesine. Five minutes later, 1250 ml. of methylene dichloride are added. After mixing thoroughly, the organic layer is separated and the aqueous layer washed twice with 500 ml. portions of methylene dichloride. The methylene dichloride extracts are combined and the combined extracts evaporated to dryness. The resulting residue is dissolved in 782 ml. of 1 N aqueous hydrochloric acid. The acidic layer is extracted with 1000 ml. of methylene dichloride. The acidic layer is extracted twice more with 200 ml. portions of methylene dichloride. The organic extracts are combined and the combined extracts washed with 200 ml. water. This aqueous extract is combined with the acidic aqueous layer which is then made basic by the addition of 14 N aqueous ammonium hydroxide (400 ml). The resulting suspension is extracted with, successively, 1250, 300 and 300 ml. portions of methylene dichloride. The organic extracts are combined and the combined extracts in turn washed with 300 ml. of saturated aqueous sodium chloride and then dried. Evaporation of the organic solvent yields vindesine base. Yield = 75–81% by weight.

Vindesine thus prepared is purified by chromatography over silica gel using a methanol-diethylamine-water-methylene dichloride solvent mixture (45:10:4:45) as the eluant. The vindesine is placed on the column in methylene dichloride solution; yield of purified vindesine = 75–83%. Vindesine thus purified is crystallized from a 4.3:0.7 methanol-ethanol solvent; yield of crystalline base = 82%. The sulfate is prepared in acetonitrile solution by standard procedures. Overall yield of vindesine sulfate from VLB sulfate = about 53%.

EXAMPLE 4

Alternate Preparation of Vindesine

A slurry was prepared with 1 kg. of fresh Raney nickel and 6 l. of methanol in a 12 l. Morton flask fitted with thermometer, stirrer, and condenser. A solution of 200 g. of 4-desacetyl VLB C-3 carboxhydrazide (from Example 2) dissolved in 3 l. of methanol was added thereto. The reaction mixture was heated to reflux for about 7 hours. The reaction mixture was then filtered by decantation through about ½ inch of talc spread on a 24 cm. Buchner funnel. The Raney nickel remaining behind in the flask was washed 4–5 times with 1 liter portions of anhydrous methanol. The filtrate was evaporated to a volume of about less than 1 l. During this concentration process, 4-desacetyl VLB C-3 carboxamide thus formed began to crystallize. The solution was transferred to a flask, and the flask with contents refrigerated overnight. Filtration of the crystalline material yielded 179.4 g. (wet weight) of 4-desacetyl VLB C-3 carboxamide. The filtrate was concentrated and yielded an additional 53.3 g. of compound (wet weight). Total yield equals 86.9 percent.

EXAMPLE 5

Preparation of Salts

Other salts, including salts with inorganic anions such as chloride, bromide, phosphate, nitrate and the like as well as salts with organic anions such as acetate, chloroacetate, trichloroacetate, benzoate, alkyl or aryl sulfonates and the like, are prepared from vindesine base by a procedure analogous to that set forth in Example 1 above for the preparation of the sulfate salt by substituting the appropriate acid in a suitable diluent in place of the 2 percent aqueous sulfuric acid of that example.

Vindesine has been shown to be active against transplanted mouse tumors in vivo, particularly Ridgway osteogenic sarcoma (ROS) and Garnder lymphosarcoma (GLS). In demonstrating activity of vindesine against these and other tumors, a protocol was used which involved the administration of the drug, usually by the intraperitoneal route, at a given dose level for 7–10 days after inoculation with the tumor.

The following table—Table 1—gives the results of several experiments in which mice bearing transplanted tumors were treated successfully with vindesine. In the table, column 1 gives the name of the compound; column 2, the transplanted tumor; column 3, the dose level or dose level range and the number of days the dosage was administered; and column 4, the percent inhibition of tumor growth/or percent prolongation of survival time. (ROS is an abbreviation for Ridgway osteogenic sarcoma; GLS for Gardner lymphosarcoma; and P1534 (J) for a leukemia.

TABLE 1

| Compound | Tumor | mg/kg. × days | Percent Inhibition |
| --- | --- | --- | --- |
| 4-Desacetyl VLB C-3 carboxamide sulfate | GLS | 0.15–1.0 × 10 | 79–100 |
| | ROS | 0.15–0.4 × 10 | 49–100 |
| | P1534 (J) (S. C.) | 0.2–0.25 × 10 | 36–37 |

As would be expected, vindesine differs in its antitumor spectrum from VLB, leurocristine and leurosine, as well as from the C-4 N,N-dialkylglycyl esters of VLB in the same way that the anti-tumor spectra of those compounds differ among themselves, some being more effective against certain tumors or classes of tumors and less effective against others. However, in utilizing vindesine clinically, the oncologist would administer it initially by the same route in the same vehicle as for clinical use of leurocristine and VLB for treatment of acute lymphatic leukemia, acute granulocytic leukemia, chronic myeloid leukemia, non-small cell lung cancer, Hodgkin's disease, non-Hodgkin's lymphoma, malignant melanoma, carcinoma of the breast, esophageal carcinoma and testicular carcinoma. Differences in dosage level would, of course, be based on relative activity between leurocristine and vindesine in the same experimental tumor in mice. Vindesine of this shows decreased neurotoxicity compared with leurocristine, and some vincristine-resistant neoplasms are susceptible to vindesine.

In utilizing vindesine as an anti-neoplastic agent, either the parenteral or oral route of administration may be employed. For oral dosage, a suitable quantity of a pharmaceutically-acceptable salt of vindesine formed with a non-toxic acid is mixed with starch or other excipient and the mixture placed in telescoping gelatin capsules each containing from 7.5-50 mg. of active ingredients. Similarly, the anti-neoplastically active salt can be mixed with starch, a binder, and a lubricant and the mixture compressed into tablets each containing from the 7.5-50 mgs. of salt. The tablets may be scored if lower or divided dosages are to be used. For this use particularly iv, isotonic solutions are employed containing 1-10 mg./ml. of a salt of vindesine. Vindesine sulfate is administered at the rate of from 0.01 to 1 mg./kg. and preferably from 0.1 to 1 mg./kg. of mammalian body weight once or twice a week or every two weeks depending on both the activity and the toxicity of the drug. An alternative method of arriving at a therapeutic dose is based on body-surface area with a dose in the range 1 to 10 mg./meter squared of mammalian body surface every 7 or 14 days.

Vindesine is presently undergoing a clinical trial in humans against selected malignancies, specifically acute lymphatic leukemia, acute granulocytic leukemia, chronic myeloid leukemia, non-small cell lung cancer, Hodgkin's disease, non-Hodgkin's lymphoma, malignant melanoma, carcinoma of the breast, esophageal carcinoma and testicular carcinoma. The clinical trial is being carried out in accordance with a procedure suggested by S. K. Carter in a section headed "Study Design Principles for the Clinical Evaluation of New Drugs as Developed by the Chemotherapy therapy Programme of the National Cancer Institute" to be found on pages 242-289 of a recent book "The Design of Clinical Trials in Cancer Therapy" edited by Maurice Staquet (Futura Publishing Co., New York, 1973). The above section refers to 10 "signal" tumors which have been designated by the National Cancer Institute as those tumors against which clinical trial candidates should be screened. These include adenocarcinoma of the breast, adenocarcinoma of the colon, bronchogenic carcinoma, adenocarcinoma of the pancreas, ovarian cancer, malignant melanoma, acute myelocytic leukemia, acute lymphocytic leukemia, lymphomatous disease and malignant glyoma. Vindesine has been subjected to pharmacokinetic studies by Nelson, et al. and by Owellen, et al. *Procedings American Association for Cancer Research, Abstracts Nos.* 118 and 406 (May 4-8, 1976). In these studies, vindesine was administered to patients with advanced cancer at a dose level of 2-3 mg./square meter of body surface by the intravenous route. A radioimmunoassay employing antibodies to an antigen prepared by reacting 4-desacetyl VLB C-3 carboxazide with protein was employed to determine blood levels. The above dose levels were on a weekly basis and during this study, divided dosages of 1 to 1 ½ mg. per square meter of body surface were given on a semi-weekly basis. These pharmacokinetic studies demonstrated that doses of that magnitude did not show undue signs of toxicity. Clinical trial was then initiated by two different groups which reported their results at the same meeting (*id Abstracts No.* 510 and 694.) In one of these studies, dosages of vindesine by the intravenous route varying from 2 to 12.5 mg. over each 7 or 14 days produced a number of physiological effects. It is believed that dosages of 8 mg./square meter or larger would cause undue toxicity. At the lower dosage rates, two out of nine patients with acute leukemia achieved partial remissions and one out of four patients with squamous cell carcinoma and one out of four with renal cell carcinoma achieved some response. No response was seen in a number of other malignancies. In the second study, vindesine was given at doses ranging from 0.5-6 mg/square meter to 42 adults and 9 children. None of the children developed neurotoxicity. Minor response was seen in a variety of tumors. In further studies carried out by Richard W. Dyke, M.D. of the Lilly Laboratory for Clinical Research, Indianapolis, Ind., Administration of vindesine in the same dosage range was able to maintain an adult with an acute leukemia in remission (produced by other agents) for a 3-4 month period. An initial (partial) response was also seen in a malignant melanoma after 8 doses. Both of these patients are still being carried on vindesine. It is expected that further clinical results will be forthcoming from this trial of vindesine in human neoplasms. Vindesine has recently been the subject of a Workshop at Frankfurt, Germany (July 7, 1978) and the papers presented at that Workshop have been collected in *Cancer Chemotherapy and Pharmacology*, 2 (No. 4), 229-274 (1979).

The first paper in this collection, by Dyke et al., gives a summary of clinical trial data in humans with vindesine, pages 230-1, starting right-hand column, third paragraph. These data indicate that vindesine gives a 40 percent remission rate in acute lymphatic leukemia (most of whom were resistant to all previously available efficient drugs, including vincristine), 30 percent response in acute myelomonocytic leukemia, Hodgkins lymphoma, 36-57 percent response in breast cancer (depending on degree of tissue involvement), 22 percent response in lung cancer, (45 percent with combination of vindesine and cis-platinum) plus responses in testicular carcinoma, esophageal carcinoma and melanoma. The 44 reference bibliography should also be noted. Other papers deal with toxicity problems (Obrist et al., King et al.); clinical trial (Bayssas et al.—the Mathe group; Retsas et al.; Smith et al.; Bedikian et al.; Krivit et al.) and pharmacokinetics (Nelson et al.).

The last paper, a short communication by Gralla et al. (Sloan-Kettering) mentions the enlistment of 275 patients in a phase II clinical trial with *major, objective responses* seen in bronchogenic carcinoma (small cell and non-small cell), melanoma, testicular carcinoma, esophageal carcinoma, acute lymphocytic leukemia, malignant lymphoma and Wilms' tumor. Minor responses were seen in breast carcinoma, renal cell carcinoma, ovarian carcinoma, soft-tissue sarcoma, head and neck epidermoid carcinoma, mesothelioma and choriocarcinoma.

The summary (page 274) begins with these words: "The early results of phase-II trials of vindesine have shown evidence of antineoplastic activity in several diseases".

It is apparent that vindesine as the sulfate salt is active against a wide variety of neoplasms, specifically acute lymphatic leukemia, acute granulocytic leukemia, chronic myeloid leukemia non-small cell lung cancer, Hodgkin's disease, non-Hodgkin's lymphoma, malignant melanoma, carcinoma of the breast, esophageal carcinoma and testicular carcinoma. As clinical experience with vindesine alone or in combination with other antineoplastics is gained, a group of vindesine-susceptible neoplasms will be characterized and it is this group of tumors against which vindesine will be used. As previously stated, this group of vindesine susceptible neoplasms includes some vincristine-resistant neoplasms. Secondly, there will be neoplasms against which vindesine has only marginal activity, but vindesine will be used against such neoplasms as part of a combination therapy regimen which combination may include only one other oncolytic agent such as cisplatinum or it may be a shotgun type therapy in which other agents include an alkylating agent and an antimetabolite. Thus the term "vindesine-susceptible neoplasm" includes both those neoplasms against which vindesine has shown primary activity and those neoplasms against which a combination of oncolytic agents is used, said combination including vindesine.

Vindesine is currently approved for marketing in France and in England.

I claim:

1. A pharmaceutical preparation in dosage unit form adapted for intravenous administration comprising per dosage unit an effective amount within the range 1 to 10 mg/ml of vindesine or a pharmaceutically-acceptable acid addition salt plus a pharmaceutical excipient thereof.

2. A dosage form according to claim 1 in which vindesine is present as the sulfate salt.

3. The method of treating neoplasms which comprises administering to a mammal suffering from a vindesine-susceptible neoplasm selected from the group consisting of acute lymphatic leukemia, acute granulocytic leukemia, chronic myeloid leukemia, non-small cell lung cancer, Hodgkin's disease, non-Hodgkin's lymphoma, malignant melanoma, carcinoma of the breast, esophageal carcinoma and testicular carcinoma an anti-neoplastically-effective amount of vindesine or a pharmaceutically-acceptable acid addition salt thereof.

4. A method according to claim 3 in which vindesine monosulfate is used.

5. A method according to claim 3 in which vindesine or a salt thereof is administered at a dose level in the range 0.1–1 mg/kg of mammalian body weight.

* * * * *